United States Patent
Simpson et al.

[11] Patent Number: 6,126,635
[45] Date of Patent: *Oct. 3, 2000

[54] ADJUSTABLE TREATMENT CHAMBER CATHETER

[75] Inventors: John B. Simpson, Woodside; Scott C. Anderson, Sunnyvale, both of Calif.

[73] Assignee: Advanced Cardiovascular Systems, Inc., Santa Clara, Calif.

[*] Notice: This patent is subject to a terminal disclaimer.

[21] Appl. No.: 08/462,076

[22] Filed: Jun. 5, 1995

Related U.S. Application Data

[63] Continuation of application No. 08/128,948, Sep. 29, 1993, Pat. No. 5,462,529.

[51] Int. Cl.$^7$ .................................................. A61M 29/00
[52] U.S. Cl. .............................. 604/101; 604/22; 604/27; 604/35; 604/509; 606/170; 606/180
[58] Field of Search ....................... 604/101, 102, 604/22, 27, 43, 35, 49; 606/170, 180

[56] References Cited

U.S. PATENT DOCUMENTS

| | | | |
|---|---|---|---|
| Re. 33,569 | 4/1991 | Gifford, III et al. | 606/159 |
| 550,238 | 11/1895 | Allen, Jr. | |
| 4,573,966 | 3/1986 | Weikl et al. | 604/53 |
| 4,655,746 | 4/1987 | Daniels et al. | 604/53 |
| 4,771,774 | 9/1988 | Horzewski et al. | 128/344 |
| 4,771,777 | 9/1988 | Simpson et al. | 128/305 |
| 4,781,186 | 11/1988 | Simpson et al. | 128/305 |
| 4,794,931 | 1/1989 | Yock | 128/660.03 |
| 4,832,028 | 5/1989 | Patel | 128/344 |
| 4,883,459 | 11/1989 | Calderon | 604/28 |
| 4,911,163 | 3/1990 | Fina | 606/127 |
| 4,979,951 | 12/1990 | Simpson | 606/159 |
| 5,000,185 | 3/1991 | Yock | 128/662.03 |
| 5,007,917 | 4/1991 | Evans | 606/170 |
| 5,041,089 | 8/1991 | Mueller et al. | 604/96 |
| 5,059,178 | 10/1991 | Ya | 604/101 |
| 5,071,425 | 12/1991 | Gifford, III et al. | 606/159 |
| 5,078,722 | 1/1992 | Stevens | 606/159 |
| 5,084,010 | 1/1992 | Plaia et al. | 604/22 |
| 5,085,662 | 2/1992 | Willard | 606/159 |
| 5,087,265 | 2/1992 | Summers | 606/159 |
| 5,090,960 | 2/1992 | Don Michael | 604/101 |
| 5,092,873 | 3/1992 | Simpson et al. | 606/159 |
| 5,100,424 | 3/1992 | Jang et al. | 606/159 |
| 5,102,390 | 4/1992 | Crittendon et al. | 604/96 |
| 5,108,411 | 4/1992 | McKenzie | 606/159 |
| 5,135,484 | 8/1992 | Wright | 604/28 |
| 5,135,531 | 8/1992 | Shiber | 606/159 |
| 5,156,610 | 10/1992 | Reger | 606/159 |
| 5,158,564 | 10/1992 | Schnepp-Pesch et al. | 606/159 |
| 5,176,693 | 1/1993 | Pannek, Jr. | 606/159 |
| 5,181,920 | 1/1993 | Mueller et al. | 606/159 |
| 5,226,909 | 7/1993 | Evans et al. | 606/159 |
| 5,250,059 | 10/1993 | Andreas et al. | 606/159 |
| 5,281,200 | 1/1994 | Corso, Jr. et al. | 604/96 |
| 5,318,576 | 6/1994 | Plassche, Jr. et al. | 606/159 |

*Primary Examiner*—Wynn Wood Coggins
*Assistant Examiner*—Eric Kline
*Attorney, Agent, or Firm*—Blakely, Sokoloff, Taylor & Zafman LLP

[57] ABSTRACT

Disclosed herein is a catheter device for treatment of disease in biological conduits. The device has inner and outer coaxial catheter members, each having an inflatable balloon attached near its distal end. When the balloons are inflated, a sealed treatment chamber is created between the balloons. The length of the treatment chamber is adjustable by sliding the coaxial catheter members with respect to each other to obtain a desired separation between the attached balloons before inflation. Biological debris is trapped within the chamber and removed by infusion and aspiration of a flushing fluid, reducing the risk of myocardial infarction. Adjunctive treatment devices can be inserted into the sealed treatment chamber through a lumen of the outer coaxial member.

21 Claims, 3 Drawing Sheets

ADJUSTABLE TREATMENT CHAMBER CATHETER

CO-PENDING AND RELATED APPLICATIONS

This Application is related to U.S. application Ser. No. 08/109,215, filed Aug. 18, 1993, entitled "Treatment Chamber Catheter," which is hereby incorporated by reference as though set forth in full herein, and is a continuation of U.S. application Ser. No. 08/128,948, filed Sept. 29, 1993, now U.S. Pat. No. 5,462,529, entitled "Adjustable Treatment Chamber Catheter."

BACKGROUND OF THE INVENTION

1. Field of the Invention

This invention relates to catheters and more particularly to multiple concentric catheters having expandable balloons defining a treatment chamber.

2. Previous Art

Blood vessels at certain critical parts of the human circulatory system can and often do become burdened with deposits, coatings, occlusions, and the like (hereafter "burden") which can reduce the vessel's blood carrying capacity. In some patients, this reduced capacity can cause serious and permanent injury. As a result, when significant burden is found to exist, some form of medical intervention is often indicated.

A number of intervention techniques have been developed over the years. These techniques permit the removal or reduction of the burden so that an increased and healthier blood flow can result. When a normal flow cannot be restored by these methods, the burdened portions of the vessel are sometimes bypassed using a vessel taken from elsewhere in the body. When the original blood vessel is a coronary artery, the bypass procedure is referred to as a coronary artery bypass graft.

The bypass graft itself may in time become burdened, as was the original vessel, therefore requiring further intervention. One type of burden that is of particular concern in treatment of a bypass arises when a vein has been used to make the bypass graft. Venous grafts are particularly susceptible to deposits of a friable material which is easily loosened during an intervention.

The friable material is soft and crumbly, and pieces are easily dislodged from the inside of the bypass graft. Often a treatment site will include a high proportion of such friable material surrounding other types of burden. Under these circumstances, attempts to remove the other burden often result in much of the friable material breaking loose and entering the blood stream. This loosened biological debris can move downstream, completely blocking another portion of the artery and causing myocardial infarction.

The intervention techniques referred to above include use of known devices such as balloon angioplasty, rotational atherectomy, the transluminal extraction catheter, stents, directional coronary atherectomy, and the like. Each of these techniques, and others, is favored by practitioners in the treatment of diseased saphenous vein grafts and other vessels. Yet, each of these techniques exposes a patient to some greater or lesser degree of risk of embolism. Unfortunately, this risk is present under the most carefully conducted intervention because the friable material can be so easily dislodged.

The friable material is especially vulnerable to being dislodged from the vessel walls when a catheter is advanced across a region of diseased tissue. Consequently, catheter type treatment devices which must be repeatedly inserted and withdrawn are prone to damage or break loose such friable material. The loosened material, if not trapped in some way, is then carried away in the blood stream.

In treating diseased vessels, it will be desirable to stabilize a treatment site before proceeding with other forms of intervention. The treatment site is "stabilized" by removing as much of the friable material as possible. No current or known device satisfactorily addresses this problem.

Additionally, it is sometimes desirable to administer a medication at a localized treatment site within a vessel. However, the natural biological fluids of the vessel both dilute the medication and carry it away from the region of application.

What is needed is a device for stabilizing a treatment site by removing friable material before other intervention is begun.

Additionally, what is needed is a device for preventing loosened particles of friable material or other plaque burden from entering the blood stream.

There is a need for a device which minimizes the necessity of repeatedly passing a device through a treatment site during the course of an intervention.

There is an additional need for a device which permits a localized application of a medication at a treatment site without undue dilution or the risk of the medication entering the blood stream.

SUMMARY OF THE INVENTION

It is an object of this invention to provide a catheter device having a fluid sealed treatment chamber, including infusion and aspiration, which can be used to stabilize a treatment site.

It is an additional object of this invention to provide such a treatment chamber catheter device which remains in place at the stabilized treatment site, and which allows access by adjunctive intervention devices.

It is yet an additional object of this invention to provide a treatment chamber catheter device which allows infusion of medications, confines these to the treatment site and prevents their dilution.

In accordance with the above objects and those that will be mentioned and will become apparent below, the adjustable treatment chamber catheter of the present invention comprises:

- inner and outer coaxial catheter members, both members having a distal end and a proximal end and being slidable with respect to each other;
- two expandable sealing members, one sealing member being disposed near the distal end of each catheter member; and
- means for expanding the sealing members to form a pair of seals with the biological conduit, an adjustable length treatment chamber being defined within the conduit and between the seals,
- whereby, the adjustable treatment chamber catheter may be inserted into the biological conduit and the catheter members may be slid with respect to each other to extend the distal end of the inner catheter member beyond the distal end of the outer catheter member and to adjust the longitudinal separation between the sealing members to a predetermined distance, the sealing members then being expanded, the adjustable length treatment chamber is created within the conduit and between the seals.

In a preferred embodiment, the adjustable treatment chamber catheter according to the present invention further includes:

an intermediate coaxial catheter member located between the inner and the outer coaxial catheter members and having a distal end and a proximal end, the intermediate catheter member being slidable and rotatable with respect to the other catheter members; and burden loosening means disposed near the distal end of the intermediate catheter member for sliding and axial rotation within the treatment chamber to loosen plaque burden deposited on the biological conduit.

In another preferred embodiment, the expandable sealing members define proximal and distal ends of the treatment chamber and the device includes infusion and aspiration for flushing the treatment site and for removing biological debris from the treatment chamber.

In another embodiment of the present invention, a treatment chamber catheter for insertion into a biological conduit comprises:

a first catheter member having proximal and distal ends and an outer surface, an inflatable sealing member being disposed on the outer surface at the distal end, and an inflation lumen having an opening for communication with the sealing member and extending from the proximal end to the opening;

a second catheter member having proximal and distal ends and an outer surface, a burden loosening member being disposed on the outer surface at the distal end, and an infusion lumen extending from the proximal to the distal end and loosely enclosing the first catheter member proximal of the distal sealing member and being adapted for axial rotation about the first catheter member; and a third catheter member having proximal and distal ends and an outer surface, a proximal inflatable sealing member being disposed on the outer surface, an inflation lumen having an opening to the proximal inflatable sealing member and extending from the proximal end to the opening, and an aspiration lumen extending from the proximal end to the distal end and loosely enclosing the second catheter member proximal of the burden loosening members, a treatment chamber being defined within the conduit and between the expandable sealing members.

In a preferred embodiment, the diameter of the infusion lumen is larger than the diameter of the enclosed first catheter member. This difference in diameter allows a fluid to be passed through the infusion lumen and into the treatment chamber. The difference in diameter also permits the second catheter to be rotated at high speed about the first catheter member so that the burden loosening members can be used to remove friable tissue surrounding a lesion. The second catheter lumen is connected to an infusion port at its proximal end. The port is used to introduce a flushing fluid or liquid medication or the like into the treatment chamber.

In another preferred embodiment, the diameter of the aspiration lumen is substantially greater than the diameter of the enclosed second catheter member. The aspiration lumen is used for access by other catheter type devices to the treatment chamber and to extract excess fluid and biological debris. The infusion and aspiration lumens are connected to infusion and aspiration ports at their proximal ends.

It is an advantage of this invention to provide a catheter device having a treatment chamber whose length can be easily adjusted to seal a specific region of a blood vessel only.

It is an additional advantage of this invention to trap loosened particles and thereby to reduce a risk of embolism.

It is also an advantage of this invention to stabilize a treatment site in saphenous vein graft repair.

It is yet another advantage of this invention to confine an infused medication to a treatment site and to prevent dilution or the carrying away into the blood stream of the medication.

It is an additional advantage of this invention to provide an adequately flushed and aspirated treatment chamber.

It is an advantage of this invention to remain in place while other interventions use the treatment chamber.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

The words "proximal" and "distal," as used below, have the following meaning, the "proximal" end of the catheter device is the end farthest from the treatment chamber, while the "distal" end is the end closest to the treatment chamber and includes the parts illustrated in the drawing.

The phrases "blood vessel" and "biological conduit" are used interchangeably throughout. Though typically the treatment chamber catheter 10 will be employed within a blood vessel, it is not to be so limited. In general it can be used within any biological vessel or conduit of a body.

The invention will now be described with respect to FIG. 1, which illustrates the adjustable treatment chamber catheter, identified generally by the numeral 10, in accordance with the present invention. The adjustable treatment chamber catheter 10 includes concentric first, second and third catheter members, 12, 28 and 40, respectively, a distal expandable sealing member 20, a proximal expandable sealing member 48, and burden loosening members 38.

Figure 1:
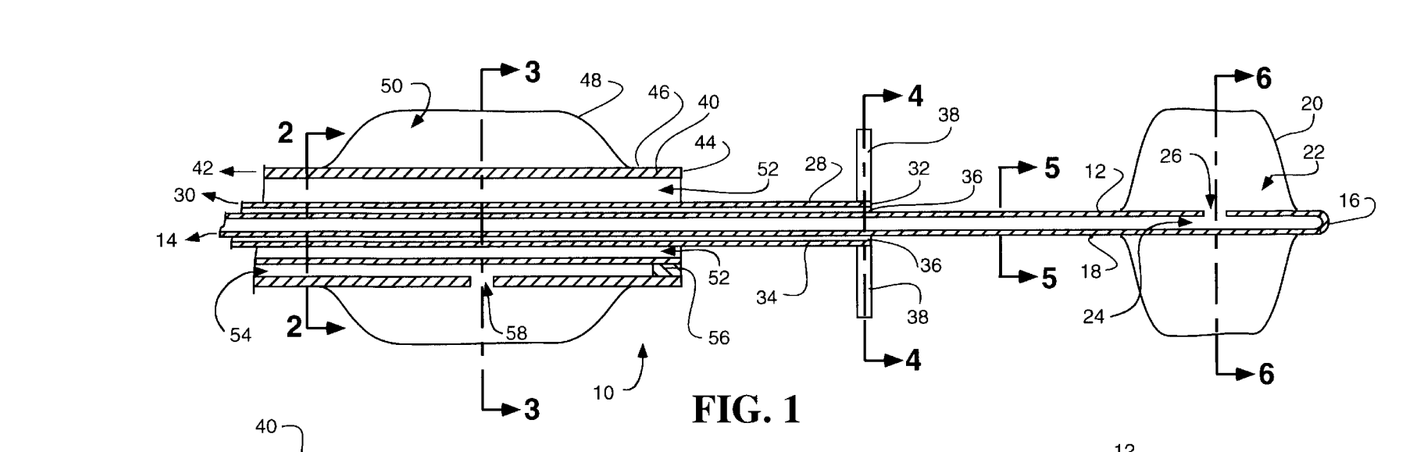
FIG. 1 is a partial side view of the adjustable treatment chamber catheter according to the present invention.

As illustrated in FIG. 1, each of the three concentric catheter members 12, 28 and 40, extends progressively beyond a distal end of the enclosing catheter member. The proximal expandable sealing member 48 is attached near the distal end of the third catheter member 40. The burden loosening members 38 are attached to the second catheter member 28 near its distal end. The distal expandable sealing member 20 is attached near the distal end of the first catheter member 12. The first and third catheter members, 12, 40, may be adjusted axially with respect to one another to adjust the separation between the distal and proximal expandable sealing members, 20, 48. The expandable sealing members will be inflated to form fluid seals with the walls of a biological conduit. The second catheter member 28 and attached burden loosening members 38 will be rotated at high speed allowing the burden loosening members to loosen and remove diseased tissue. The loosened and removed tissue will be confined between the inflated sealing members, 20, 48.

The adjustable treatment chamber catheter 10 includes a first catheter member 12 having a proximal end 14 and a distal end 16. The first catheter member 12 has an outer surface 18 and a distal expandable sealing member 20 which is attached circumferentially on the outer surface 18 near the distal end 16. The distal expandable sealing member 20 has an interior 22. The first catheter member 12 also includes a first lumen 24 extending between the proximal and distal ends, the first lumen 24 having an opening 26 to the interior 22 of the distal expandable sealing member 20 for inflation of the member 20. The first lumen 24 terminates in a closure (shown generally as the distal end 16) distally of the opening 26.

A second catheter member 28 has a proximal end 30, a distal end 32, and an outer surface 34. The second catheter member 28 has a second lumen 36 extending between the proximal end 30 and the distal end 32 and loosely enclosing the first catheter member 12 from a point near its proximal end 14 to a point proximal to the distal expandable sealing member 20. The second catheter member 28 includes a plurality of burden loosening members 38 which are radially disposed on the outer surface 34 near the distal end 32.

A third catheter member 40 has a proximal end 42, a distal end 44, and an outer surface 46. The third catheter member 40 includes a proximal expandable sealing member 48 which is attached circumferentially to the outer surface 46 near the distal end 44. The proximal expandable sealing member 48 has an interior 50. A third lumen 52 extends between the proximal and distal ends of the third catheter member 40 and has a diameter which is substantially larger than the diameter of the enclosed second catheter member 28. The third lumen 52 encloses the second catheter member 28 from a point near the proximal end 30 to a point proximal to the burden loosening members 38. A fourth lumen 54 extends between the ends of the third catheter member 40 and has an opening 58 to the interior 50 of the proximal expandable sealing member 48 for inflation of the member 48. The fourth lumen 54 terminates in a closure 56 distally of the opening 58.

FIGS. 2–6 are cross-sectional views taken at corresponding lines through the partial catheter shown in FIG. 1 looking in the direction of the arrows.

Figures 2, 3:
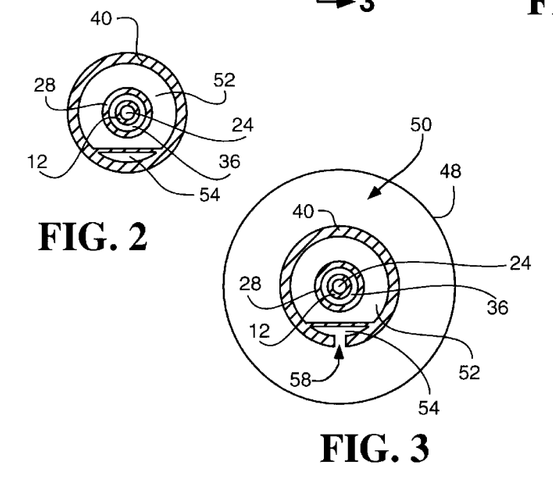
FIGS. 2–6 are cross-sectional views taken through FIG. 1 in the direction of the arrows.

With particular reference to FIG. 2, the concentric catheter members are shown to have a generally circular cross-section. The first catheter member 12 includes the first lumen 24. The second lumen 36 of the second catheter member 28 is slightly greater in diameter than the first catheter member 12, which it encloses. The third lumen 52 of the third catheter member 40 is substantially greater in diameter than the second catheter member 28, which it encloses. A fourth lumen 54 is shown.

With particular reference to FIG. 3, there is illustrated a cross-section through the proximal expandable sealing member 48 and the inflation opening 58 of FIG. 1. The interior 50 of the proximal expandable sealing member 48 communicates with the fourth lumen 54 via the opening 58.

Figures 4, 5, 6:
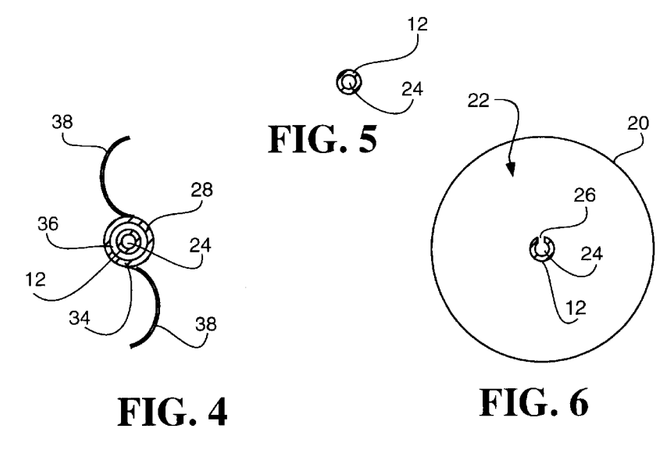

With particular reference to FIG. 4, there is illustrated a cross-section taken at the line 4—4 of FIG. 1 and illustrates two burden loosening members 38 radially attached to the outer surface 34 of the second catheter member 28. The second catheter member 28 is no longer enclosed by the third lumen 52 of the third catheter member 40, and is shown extending distally of the distal end 44 of the third catheter member 40.

With particular reference to FIG. 5, there is illustrated a cross-section through the first catheter member 12 of FIG. 1 showing the first lumen 24. The second lumen 36 of the second catheter member 28 no longer encloses the first catheter member 12.

With particular reference to FIG. 6, this is an illustration of a cross-section taken through the distal expandable sealing member 20 and the inflation opening 26 of FIG. 1. The interior 22 of the distal expandable sealing member 20 communicates with the first lumen 24 via the opening 26.

In Use

The adjustable treatment chamber catheter 10 is indicated for the treatment of saphenous vein grafts where the removal of friable material within a sealed treatment chamber can be accomplished with minimum risk of embolization. Once the treatment site has been stabilized, other forms of treatment can be used in conjunction with the present invention.

The present invention will now be described with reference to a typical intervention. A guiding catheter (not shown) will be introduced first via a femoral artery into the aorta. A guiding catheter has a single large lumen used for insertion of other catheter devices. The guiding catheter will then be left in place throughout the remainder of the intervention and will provide a safe and rapid access to the aorta region.

Next, the adjustable treatment chamber catheter 10 will be inserted through the guiding catheter and into a selected coronary bypass graft or artery. Fluoroscopy is typically used to guide the distal end of the catheter 10 to the desired treatment site.

When the situation at the treatment site permits, the location of the expandable sealing members 20, 48 will be adjusted to establish a treatment chamber of the desired length, with one sealing member located distally of the site and the other located proximal of the site, and a desired distance apart. The expandable sealing members 20, 48 will be inflated so that they form a fluid seal with the walls of the vessel and create the treatment chamber around the site.

Figure 7:
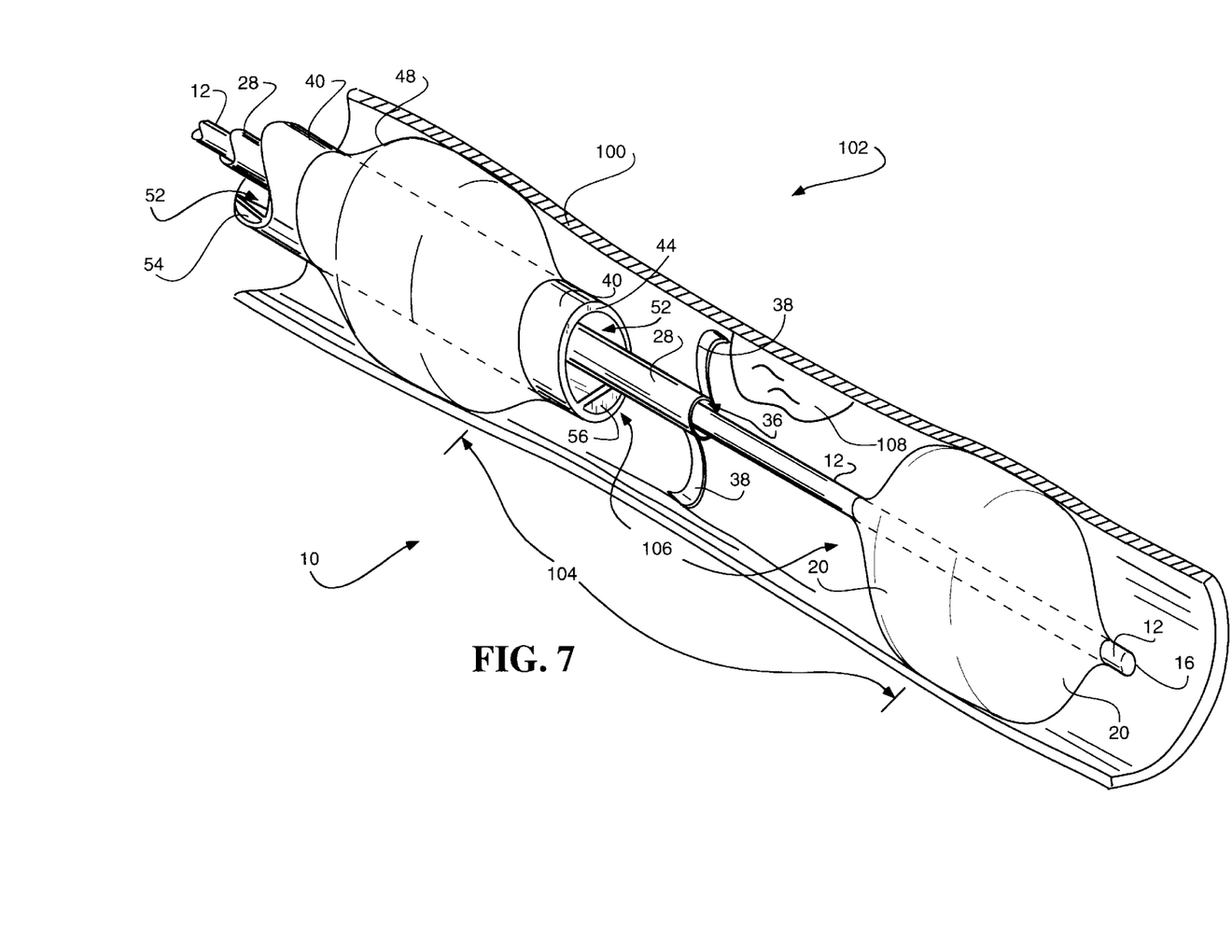
FIG. 7 is a partial perspective oblique view of the treatment chamber catheter illustrated in FIG. 1 deployed inside a blood vessel.

FIG. 7 illustrates the treatment chamber 106 established at a treatment site 102 inside a vessel 100. The expandable sealing members 20, 48 are shown in the inflated condition, forming fluid seals with the walls of the vessel 100. Friable material 108 is shown attached to a wall of the vessel 100 at the treatment site 102. To loosen or remove the friable material 108, the second catheter member 28 is rotated at a high speed, and its longitudinal position is adjusted to bring the burden loosening members into contact with the material 108.

Infusion of a flushing fluid is made through the second lumen 36 from an infusion port (not shown) located at the proximal end 30 of the second catheter member 28. Loosened particles of friable material and excess fluid are removed from the treatment chamber 106 back through the third lumen 52 and an aspiration port (not shown).

The diameter of the second lumen 36 exceeds the diameter of the first catheter member 12 just sufficiently to permit infusion to occur at a useful rate, and for the second catheter member 28 to rotate freely about the first catheter member 12.

The diameter of the third lumen 52 substantially exceeds the diameter of the second catheter member 28 so that aspiration of particles of loosened friable material and excess fluid can occur at a rate corresponding to the infusion rate. In general, the size of the particles will permit aspiration in the manner described. When the size of the particles otherwise prevents removal by aspiration as described, the diameter of the third lumen 52 will permit insertion of another catheter device used to further reduce the size of the particles.

Sealed Treatment Chamber

The two inflated expandable sealing members 20,48 prevent the release of loosened friable material from the treatment chamber 106 into the normal blood stream of the vessel 100. The risk that such particles might be carried away into the circulatory system and form emboli is greatly reduced, though not entirely eliminated. Such particles can still enter the blood stream and pose a risk whenever the treatment chamber catheter 10 is being positioned or repositioned. This occurs during such times because the expandable sealing members are not inflated and therefore do not form a fluid seal with the walls of the vessel, and also because the device must be passed across a lesion at a new treatment site.

The existence of a sealed treatment chamber 106 having infusion and aspiration and an access lumen (the third lumen 52) of substantial diameter create a safe and flexible environment within which to perform additional intervention. Once the treatment site 102 has been stabilized by a removal of a majority of the unstable friable material 108, other burden can be addressed using preferred intervention techniques, such as balloon angioplasty, rotational atherectomy, the transluminal extraction catheter, stents, directional coronary atherectomy, and the like. Each of these techniques, used in the absence of the sealed treatment chamber 106, encounters some difficulty in preventing the escape of particles into the blood stream. These are not only particles of accidentally loosened friable material, as in a vein graft repair, but include particles of other types of burden removed as a primary object of the intervention.

Thus, the sealed treatment chamber 106 provides an accessible and continually flushed environment for adjunctive treatment of arterial heart disease. The sealed treatment chamber substantially reduces the risk of embolism.

Medications

The sealed treatment chamber 106 also allows the introduction of specific medications by infusion to the treatment site 102. Such medications are confined at the treatment site 102. Normally, a medication in the form of a fluid could not be applied at a treatment site because there would be no practical way to prevent the medication from being carried away in the blood stream. The two expandable sealing members 20, 48 form fluid seals with the walls of a vessel 100, however, and thus effectively confine a medication to the treatment chamber 106. The medication can thus be applied in undiluted form directly at the treatment site 102. This ability to confine the application and to prevent dilution, greatly enhances the effectiveness of such treatment.

Alternative Embodiments

Figure 8:
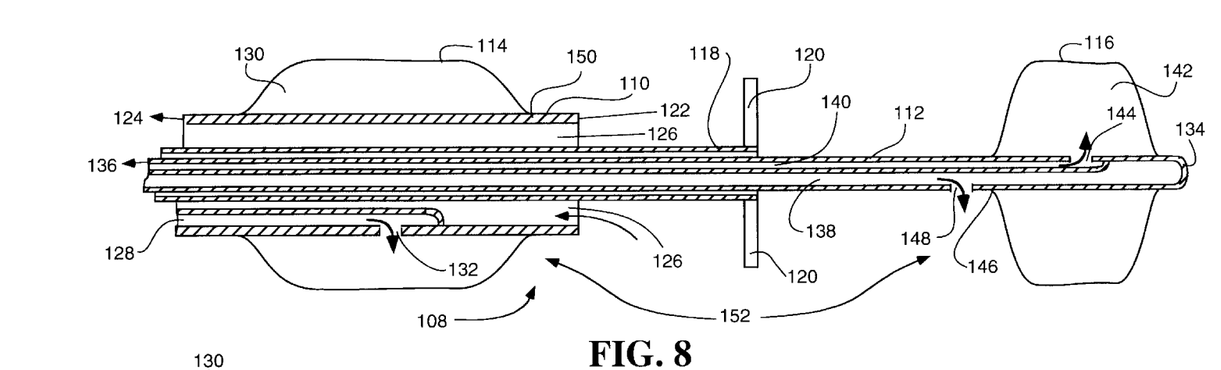
FIG. 8 is a partial side view of the adjustable treatment chamber catheter including an infusion lumen and an infusion opening near the distal end of the treatment chamber.

FIG. 8 illustrates a partial side view of an alternative embodiment of the treatment chamber catheter in accordance with the present invention. The arrangement for infusion of fluid into the treatment chamber provides flow from the distal end of the chamber toward the proximal end. This embodiment eliminates the need for an additional pressurized, rotating seal near the proximal end of the catheter device (not shown).

The alternative treatment chamber catheter 108 includes an outer coaxial catheter member 110, an inner coaxial catheter member 112, a pair of expandable sealing members 114, 116, an intermediate coaxial catheter member 118, and burden loosening members 120.

The outer coaxial catheter member 110 has a distal end 122 and a proximal end 124. The expandable sealing member 114 is disposed on the outer coaxial catheter member 110 near the distal end 122. The outer coaxial catheter member 110 includes an access and aspiration lumen 126, and an inflation lumen 128. The expandable sealing member 114 has an interior 130 for receiving and storing a fluid during expansion. An opening 132 connects the inflation lumen 128 with the interior 130. The inflation lumen 128 extends from the proximal end 124 to the opening 132. During expansion of the expandable sealing member 114, a fluid is introduced at the proximal end of the inflation lumen 128. The fluid travels along the lumen 128, then through the opening 132 and into the interior 130, urging the expandable sealing member 114 against the walls of the biological conduit (not shown).

The inner coaxial catheter member 112 has a distal end 134 and a proximal end 136. The expandable sealing member 116 is disposed on the inner coaxial catheter member 112 near the distal end 134. The inner coaxial catheter member 112 includes an infusion lumen 138 and an inflation lumen 140. The expandable sealing member 116 has an interior 142 for receiving and storing a fluid during expansion. An opening 144 connects the inflation lumen 140 with the interior 142. The inflation lumen 140 extends from the proximal end 136 to the opening 144. The expandable sealing member 116 has a proximal end 146. The inner coaxial catheter member 112 includes an infusion opening 148 located near the proximal end 146 of the sealing member 116. A fluid is introduced at the proximal end of the infusion lumen 138, travels along lumen 138, then through the infusion opening 148 (shown with arrow).

The expandable sealing member 114 has a distal end 150. A sealed treatment chamber 152 is defined between the expanded sealing members 114, 116. The access and aspiration lumen 126 extends from the proximal end 124 to the distal end 122 of the outer coaxial catheter member 110, opening into the treatment chamber 152. Excess fluid and biological debris are removed from the treatment chamber 152 through the access and aspiration lumen 126 (shown with arrow).

Figures 9, 10:
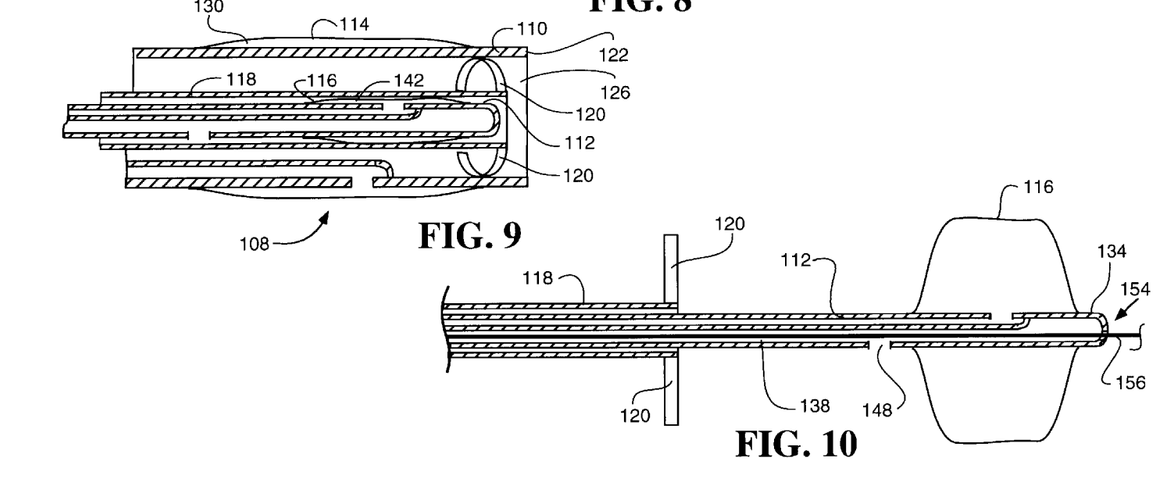
FIG. 9 is a partial side view of the apparatus illustrated in FIG. 8 showing coaxial catheter members being withdrawn into an outer catheter member.
FIG. 10 is a partial side view of the apparatus shown in FIG. 8 and including a guide wire.

FIG. 9 is a partial side view of the apparatus illustrated in FIG. 8. The inner coaxial and the intermediate coaxial catheter members 112,118 are shown slid proximal of the distal end 122 of the outer coaxial catheter member 110. The expandable sealing members 114,116 are shown deflated, the inflation fluid having been withdrawn from interiors 130,142. The burden loosening members 120 are shown folded within the distal end of the access and aspiration lumen 126. In this configuration, the catheter device 108 can be inserted, removed and repositioned within a biological conduit.

In another alternative embodiment, FIG. 10 is a partial side view of a treatment chamber catheter including a guide wire 156. The infusion lumen 138 includes a small opening 154 at the distal end 134. The guide wire 156 extends through the infusion lumen 138, then passes through the small opening 154, extending distally of the distal end 134. The guide wire 156 is slidable within the infusion lumen 138. The fit of the small opening 154 is adapted to allow the guide wire 156 to slide within the opening 154 while not allowing infusion fluid to pass beyond the distal end 134 and into the blood stream.

In another alternative embodiment, perfusion can be added by bypassing the treatment chamber with a perfusion lumen (not shown). This allows some blood to continue to flow within the vessel and around the sealed treatment chamber, reducing ischemic stress and permitting an intervention of longer duration.

A Treatment Method

The present invention readily lends itself to the treatment of atherosclerotic vessels. A method for conducting such treatment is defined which begins with a step of providing a treatment chamber catheter of the type described above.

The method continues with the steps of guiding the treatment chamber catheter into the biological conduit. Then determining a location of a treatment site. This step is usually accomplished by means of fluoroscopy and radio opaque dyes. Next, the distal sealing member is positioned distally to the selected treatment site, and the proximal sealing member is positioned proximal of the selected site. The separation of the two sealing members is adjusted by sliding the catheter members with respect to one another. Then, the sealing members are inflated to seal off the region of the conduit surrounding the site (see FIG. 7). Finally, a flushing fluid is passed through the sealed region by means of infusion and aspiration.

Having established a sealed, flushed treatment chamber, it is now desirable to operate the second catheter member 28 (FIG. 7) to cause the burden loosening members 38 to engage the friable material 108. It is desirable to remove as much of this material as possible from the site before beginning other types of treatment. The loosened material will be trapped within the treatment chamber 106 and will then be removed by aspiration back through lumen 52.

Now that a stabilized treatment region has been prepared, another adjunctive treatment device can be inserted into the treatment chamber 106 (not shown).

As a preliminary step, a guiding catheter might be inserted between a point of entry into the body and a region near the treatment site. For example, the guiding catheter might be inserted between a point of entry at the groin and extend to the aorta (not shown).

While the foregoing detailed description has described several embodiments of the adjustable treatment chamber catheter device 10 in accordance with this invention, it is to be understood that the above description is illustrative only and not limiting of the disclosed invention. It will be appreciated that the specific arrangement of the burden loosening members can be different from that shown in the drawing and that the relative difference in diameter of the various lumens and catheter members can differ from the examples shown in the accompanying figures and remain within the scope and spirit of this invention. Also, it will be appreciated that the device can be used within any biological conduit of the body rather than being limited to use in a blood vessel. Thus the invention is to be limited only by the claims as set forth below.

What is claimed is:

1. A method for treating a diseased biological conduit, the method comprising the steps of:
providing a treatment chamber catheter of the type having concentric catheter members, two concentric members each having a distal end including an inflatable balloon for creating a sealed treatment chamber within the biological conduit and between the balloons, the length of the treatment chamber being adjustable by sliding the two concentric catheter members with respect to each other, the treatment chamber catheter also including an intermediate concentric catheter member having a distal end including burden loosening means, the treatment chamber catheter further including both infusion and aspiration means for removing biological debris and excess fluid from the treatment chamber, access to the sealed treatment chamber by adjunctive catheter-type treatment devices being through a lumen;
guiding the treatment chamber catheter into the biological conduit;
selecting a location of a treatment site;
positioning one inflatable sealing member within the conduit distally of the selected treatment site;
positioning the other inflatable sealing member within the conduit proximally to the selected treatment site;
adjusting the separation between the inflatable sealing members by sliding said members with respect to each other;
inflating the sealing members to create a sealed treatment chamber within the conduit and between the sealing members;
introducing a fluid into the chamber via the infusion means;
loosening friable tissue at the treatment site by operating the catheter member including the burden loosening means; and
removing biological debris and excess fluid from the sealed treatment chamber via the aspiration means.

2. The method as set forth in claim 1, further including the step of inserting a guiding catheter from a point of entry into the body to a region near the treatment site and continuing with the step of guiding the treatment chamber catheter through the guiding catheter and then into the biological conduit.

3. The method as set forth in claim 2, further including the point of entry being the groin, a distal end of the guiding catheter being advanced into the aorta, and the treatment site being located in a peripheral blood vessel of the heart.

4. The method as set forth in claim 1, further including a step, immediately following the step of loosening friable material at the treatment site, of operating the catheter member including the burden loosening means to reduce the size of the loosened biological material for stabilizing the treatment site.

5. The method as set forth in claim 4, further including the steps of inserting an adjunctive catheter device for treatment into the sealed treatment chamber through the access lumen and operating the inserted device within the sealed treatment chamber to provide a predetermined adjunctive treatment.

6. The method as set forth in claim 5, wherein the predetermined adjunctive treatment includes one or more of the following: balloon angioplasty, rotational atherectomy, transluminal extraction, and directional atherectomy.

7. The method as set forth in claim 4, wherein the step of operating the catheter member including the burden loosening means includes the steps of rotating and reciprocally sliding the intermediate coaxial catheter member axially with respect to the inner coaxial catheter member.

8. The method as set forth in claim 1, wherein the selected treatment site is a saphenous vein graft.

9. A method for treating a diseased biological conduit, the method comprising the steps of:
providing a treatment chamber catheter of the type having concentric catheter members, two concentric members each having a distal end including an inflatable balloon for creating a sealed treatment chamber within the biological conduit and between the balloons, the length of the treatment chamber being adjustable by sliding the two concentric catheter members with respect to each other, the treatment chamber catheter also including an intermediate concentric catheter member having a distal end including burden loosening means, the treatment chamber catheter further including both infusion and aspiration means for removing biological debris and excess fluid from the treatment chamber, access to the sealed treatment chamber by adjunctive catheter-type treatment devices being through a lumen;

inserting the treatment chamber catheter into the body at an entry point and guiding the catheter through biological conduits toward a preselected treatment site;

establishing a sealed treatment chamber of appropriate length at the site by positioning one balloon distally and the other proximally of the site, then adjusting the distance between the balloons by sliding one balloon with respect to the other to define the length of the sealed chamber, and inflating the balloons to create a sealed chamber within a biological conduit and between the inflated balloons;

stabilizing the treatment site by operating the intermediate concentric catheter and burden loosening means to loosen friable biological material at the site, and to reduce the size of the loosened material and by flushing the loosened and reduced material from the sealed chamber via the infusion and aspiration means;

performing an adjunctive treatment at the site; and removing the treatment chamber catheter from the body.

10. The treatment method as set forth in claim 9, wherein the adjunctive treatment includes introducing a medicating fluid into the sealed treatment chamber via the infusion means, confining the medicating fluid at the treatment site, and removing the fluid from the treatment chamber via the aspiration means.

11. The treatment method as set forth in claim 10, further including the steps of preventing the fluid from being diluted and carried away in the bloodstream by confining the medicating fluid within the fluid sealed treatment chamber.

12. The treatment method as set forth in claim 9, wherein the adjunctive treatment includes balloon angiolplasty, rotational atherectomy, transluminal extraction, and directional coronary atherectomy.

13. The treatment method as set forth in claim 9, further including the steps of repositioning the sealed treatment chamber to another treatment site by deflating the balloons, guiding the treatment chamber catheter to the other treatment site, and resuming with the step of establishing a sealed treatment chamber of appropriate length.

14. The treatment method as set forth in claim 9, further including the steps of preventing debris from entering the bloodstream and causing myocardial infarction by trapping the debris between the inflated balloons within the fluid sealed treatment chamber.

15. A method for treating a diseased biological conduit, the method comprising the steps of:

providing a treatment chamber catheter of the type having concentric catheter members, two concentric members each having a distal end including an inflatable balloon for creating a sealed treatment chamber within the biological conduit and between the balloons, the length of the treatment chamber being adjustable by sliding the two concentric catheter members with respect to each other, the treatment chamber catheter also including an intermediate concentric catheter member having a distal end including burden loosening means, the treatment chamber catheter further including both infusion and aspiration means for removing biological debris and excess fluid from the treatment chamber, access to the sealed treatment chamber by adjunctive catheter-type treatment devices being through a lumen;

inserting the treatment chamber catheter into the body at an entry point;

guiding the treatment chamber catheter from the entry point into a predetermined biological conduit;

selecting a specific location of the biological conduit as a treatment site;

positioning one inflatable sealing member within the conduit distally of the selected treatment site;

positioning the other inflatable sealing member within the conduit proximally of the selected treatment site;

adjusting the separation between the inflatable sealing members by sliding said members with respect to each other;

inflating the sealing members to create a sealed treatment chamber within the conduit and between the sealing members;

operating the catheter member including the burden loosening means to loosen friable material and to reduce its size;

introducing a predetermined fluid medication via the infusion means into the sealed treatment chamber; and confining the medication at the treatment site within the sealed treatment chamber.

16. The treatment method as set forth in claim 15, further including the step of removing the confined medication and biological debris from the sealed treatment chamber via the aspiration means.

17. The treatment method as set forth in claim 16, wherein the provided treatment chamber catheter includes means for deflating the inflated sealing members, and further including the steps of deflating the inflatable sealing members and removing the treatment chamber catheter from the biological conduit.

18. The treatment method as set forth in claim 15, further including the step of inserting a guiding catheter from a point of entry into the body to a region near the treatment site and continuing with the step of guiding the treatment chamber catheter through the guiding catheter and then into the biological conduit.

19. A fluid sealed treatment chamber catheter for insertion into a biological conduit, and defining an adjustable length treatment chamber, comprising:

an inner coaxial catheter member having proximal and distal ends and including multiple lumens extending between the ends;

an outer coaxial catheter member having proximal and distal ends and including multiple lumens, the outer coaxial catheter member enclosing a portion of the inner coaxial catheter member, one lumen of the outer coaxial catheter member having a diameter and the inner coaxial catheter member having a diameter and said lumen having a diameter substantially larger than the diameter of the enclosed portion of inner coaxial catheter member;

a distal sealing member disposed near the distal end of the inner coaxial catheter member, the distal sealing member being inflatable and having an interior in fluid communication with a lumen of the inner catheter member, said lumen being sealed near the distal end of the inner coaxial catheter member permitting infusion of a fluid via said communicating lumen to inflate and aspiration of said fluid to deflate said distal sealing member;

a proximal sealing member disposed near the distal end of the outer coaxial catheter member, the proximal sealing member being inflatable and having an interior in fluid communication with a lumen of the outer catheter member, said lumen being sealed near the distal end of the outer coaxial catheter member permitting infusion of a fluid via said communicating lumen to inflate and aspiration of said fluid to deflate said proximal sealing member;

a guide wire located within a lumen and extending along a portion of, and being axially slidable with respect to the inner coaxial catheter member, the guide wire extending distally of the distal end of the inner coaxial member, said guide wire lumen forming a fluid seal with the guide wire at the distal end to the inner coaxial catheter member, the guide wire being slidable within said fluid seal, said lumen including an opening located near a proximal end of the distal sealing member; and a catheter member extending through a lumen of the outer coaxial catheter member from the proximal end to a location between the sealing members, said catheter member being rotatable and axially slidable with respect to the outer catheter member and having burden loosening members disposed near its distal end and adapted for loosening friable material.

20. The fluid sealed treatment chamber as set forth in claim 19, further including perfusion means for allowing a biological fluid to bypass the sealed treatment chamber.

21. An adjustable treatment catheter for insertion into a biological conduit, comprising:

inner and outer coaxial catheter members, both members having a distal end and a proximal end and being independently slidable with respect to each other;

two expandable sealing members, one sealing member being disposed near the distal end of each catheter member;

means for expanding the sealing members to form a pair of seals with the biological conduit, and adjustable length treatment chamber being defined within the conduit and between the seals;

burden loosening means for loosening friable material, burden loosening means positioned within the sealed treatment chamber; and perfusion means for bypassing a fluid within the biological conduit around the sealed treatment chamber.

* * * * *